(12) United States Patent
Kapoor et al.

(10) Patent No.: US 10,022,333 B2
(45) Date of Patent: Jul. 17, 2018

(54) IMAGE-GUIDED DELIVERY OF A MIXTURE OF BACTERIA AND NON-BACTERIA LINKED NANOPARTICLES

(71) Applicant: Siemens Medical Solutions USA, Inc., Malvern, PA (US)

(72) Inventors: Ankur Kapoor, Plainsboro, NJ (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 202 days.

(21) Appl. No.: 15/178,588

(22) Filed: Jun. 10, 2016

(65) Prior Publication Data

US 2017/0021041 A1 Jan. 26, 2017

Related U.S. Application Data

(60) Provisional application No. 62/173,556, filed on Jun. 10, 2015.

(51) Int. Cl.
*G06K 9/00* (2006.01)
*A61K 9/51* (2006.01)
(Continued)

(52) U.S. Cl.
CPC ............. *A61K 9/51* (2013.01); *A61B 5/055* (2013.01); *A61B 8/00* (2013.01); *A61B 34/73* (2016.02); *A61N 7/00* (2013.01); *A61B 2034/101* (2016.02)

(58) Field of Classification Search
CPC .... A61K 9/51; A61N 7/00; A61B 8/00; A61B 34/73; A61B 5/055; A61B 2034/101
See application file for complete search history.

(56) References Cited

U.S. PATENT DOCUMENTS 6,165,440 A * 12/2000 Esenaliev .............. A61K 38/19
264/473
8,915,833 B1 * 12/2014 Sahadevan ........... A61N 5/1027
600/1
(Continued)

OTHER PUBLICATIONS

Mouli et al., Image-Guided Local Delivery Strategies Enhance Therapeutic Nanoparticle Uptake in Solid Tumors, acsnano, vol. 7, No. 9, pp. 7724-7733, 2013.*

*Primary Examiner* — John Strege

(57) ABSTRACT

A computer-implemented method for image-guided delivery of a nanoparticle mixture to a target tumor located in a region of interest includes selecting a non-hypoxic delivery location within the region of interest for delivery of a non-bacteria-associated nanoparticle component included in the nanoparticle mixture and selecting a hypoxic delivery location within the region of interest for delivery of a bacteria-associated nanoparticle component included in the nanoparticle mixture. An image-guided delivery and monitoring process may then be performed. During this process intra-operative images of the region of interest are continually acquired and used to guide placement of a device into the non-hypoxic delivery location, monitor delivery of the non-bacteria-associated nanoparticle component included in the nanoparticle mixture at the non-hypoxic delivery location, guide placement of the device into the hypoxic delivery location, and monitor delivery of the bacteria-associated nanoparticle component included in the nanoparticle mixture at the hypoxic delivery location.

15 Claims, 4 Drawing Sheets

(51) Int. Cl.
*A61B 5/055* (2006.01)
*A61B 8/00* (2006.01)
*A61N 7/00* (2006.01)
*A61B 34/00* (2016.01)
*A61B 34/10* (2016.01)

(56) References Cited

U.S. PATENT DOCUMENTS

| | | | |
|---|---|---|---|
| 9,211,419 B2* | 12/2015 | Krishnan | A61N 2/002 |
| 9,636,525 B1* | 5/2017 | Sahadevan | A61N 5/1077 |
| 2005/0090732 A1* | 4/2005 | Ivkov | A61N 1/406 |
| | | | 600/411 |
| 2011/0052672 A1* | 3/2011 | Krishnan | A61K 41/0052 |
| | | | 424/450 |
| 2012/0089009 A1* | 4/2012 | Omary | A61N 1/327 |
| | | | 600/411 |
| 2012/0197060 A1* | 8/2012 | Ray | A61K 41/0085 |
| | | | 600/1 |
| 2014/0135681 A1* | 5/2014 | Angelsen | A61M 37/0092 |
| | | | 604/22 |
| 2014/0212502 A1* | 7/2014 | Liu | A61K 9/0009 |
| | | | 424/493 |

\* cited by examiner

IMAGE-GUIDED DELIVERY OF A MIXTURE OF BACTERIA AND NON-BACTERIA LINKED NANOPARTICLES

CROSS-REFERENCE TO RELATED APPLICATIONS

This application claims priority to U.S. Provisional Application Ser. No. 62/173,556 filed Jun. 10, 2015, which is incorporated herein by reference in its entirety.

TECHNICAL FIELD

The present disclosure relates generally to methods, systems, and apparatuses related to image-guided magnetic trap controlled delivery of a mixture of bacteria and non-bacteria linked nanoparticles. The techniques described herein may be applied to various imaging modalities to facilitate the delivery of compositions of such mixtures.

BACKGROUND

Current cancer therapies have limited efficacy because they are highly toxic, ineffectively target tumors, and poorly penetrate tumor tissue. Engineered nanoparticles have the unique potential to overcome these limitations by actively targeting all tumor regions and delivering therapeutic payloads.

A large body of work is dedicated to developing nanocarriers that can carry a drug payload to a target tumor and deliver this payload on a stimulus. However, it is well known that such nanocarriers that utilize the vasculature for transport may not reach the hypoxic region of the tumors which have little or poorly developed vasculature. On the other hand, nanocarriers bounded to bacteria can use the mechanism of chemotaxis, preferred growth and hypoxic germination to target mainly hypoxic regions. However, since non-hypoxic tumor compartments may not secrete specific chemoreceptors that these bacteria may bind to, such areas won't get adequate cytotoxin. Likewise, non-hypoxic regions are not favorable places for bacteria to proliferate. Further, utilizing chemotaxis as a means of transport requires tailoring each bacterium for a specific type of cancer cell, thus limiting its broader appeal.

To alleviate such limitations, a system of a mixture of nanoparticles can be delivered via the vasculature. In tumor compartments with adequate vasculature, the non-bacteria linked nanocarriers will be delivered by the usual mechanism of diffusion. For tumor compartments, the active transport mechanism of bacteria that seek anaerobic microenvironments for growth will carry the nanoparticles. For such a mixture to be an effective treatment and to minimize systemic toxicity, precise control of the time and location of the nanoparticles is crucial.

SUMMARY

Embodiments of the present invention address and overcome one or more of the above shortcomings and drawbacks, by providing methods, systems, and apparatuses related to image-guided magnetic trap controlled delivery of a mixture of bacteria and non-bacteria linked nanoparticles. In particular, the techniques described herein provide a methodology for aggregating various components and functionality to provide robust image-guided planning, guidance, monitoring and control of delivery of the nanoparticles.

According to some embodiments, a computer-implemented method for image-guided delivery of a nanoparticle mixture to a target tumor located in a region of interest includes selecting a non-hypoxic delivery location within the region of interest for delivery of a non-bacteria-associated nanoparticle component included in the nanoparticle mixture and selecting a hypoxic delivery location within the region of interest for delivery of a bacteria-associated nanoparticle component included in the nanoparticle mixture. An image-guided delivery and monitoring process may then be performed. During this process, intra-operative images of the region of interest are continually acquired and used to guide placement of a device into the non-hypoxic delivery location and monitor delivery of the non-bacteria-associated nanoparticle component included in the nanoparticle mixture at the non-hypoxic delivery location. The intra-operative images of the region of interest are also used during the process to guide placement of the device into the hypoxic delivery location and monitor delivery of the bacteria-associated nanoparticle component included in the nanoparticle mixture at the hypoxic delivery location.

In some embodiments, the aforementioned method further comprises selecting a bacteria-associated concentration value and a non-bacteria-associated concentration value based on a heterogeneity assessment of the target tumor. If concentration of the non-bacteria-associated nanoparticle component at the non-hypoxic delivery location is below the selected non-bacteria-associated concentration value, one or more concentration controlling mechanisms are used to adjust the concentration of the non-bacteria-associated nanoparticle component at the non-hypoxic delivery location. Similarly, if concentration of the bacteria-associated nanoparticle component at the hypoxic delivery location is below the selected bacteria-associated concentration value, the one or more concentration controlling mechanisms are used to adjust the concentration of the bacteria-associated nanoparticle component at the hypoxic delivery location. In embodiments where the intra-operative imaging of the region of interest is performed using a magnetic resonance imaging device, the one or more concentration controlling mechanisms may comprise a magnetic trap created by applying a gradient force toward at least one of the hypoxic delivery locations or the non-hypoxic delivery location. This magnetic trap may be generated, for example, using one or more coils from the magnetic resonance imaging device or an external field generator. In some embodiments, the non-bacteria-associated nanoparticle component and the bacteria-associated nanoparticle component of the nanoparticle mixture each comprise a carrier structure which contains a paramagnetic material. For example, in one embodiment, the paramagnetic material comprises iron oxide and the paramagnetic material is utilized by the one or more concentration controlling mechanisms.

As an alternative to magnetic resonance imaging, in other embodiments of the aforementioned method, the intra-operative imaging of the region of interest is performed using an ultrasound imaging device and the one or more concentration controlling mechanisms comprise an acoustic trap created by applying a pulse train of medium intensity ultrasound waves in a region of high concentration.

Some embodiments of the aforementioned method trigger payload release based on concentration levels. Thus, if concentration of the non-bacteria-associated nanoparticle component at the non-hypoxic delivery location is at the selected non-bacteria-associated concentration value, one or more stimuli are activated to trigger release of a non-bacteria-associated payload included in the non-bacteriaassociated nanoparticle component. Similarly, if concentration of the bacteria-associated nanoparticle component at the hypoxic delivery location is at the selected bacteria-associated concentration value, the one or more stimuli trigger release of a bacteria-associated payload included in the bacteria-associated nanoparticle component. These stimuli may comprise an energy source which applies hyperthermia to at least one of the non-hypoxic delivery locations or and the hypoxic delivery location. In one embodiment, the stimuli comprise a magnetic field.

During the image-guided delivery and monitoring process, the intra-operative images may be used to monitor release of at least one of the non-bacteria-associated payload and the bacteria-associated payload. If concentration of the released non-bacteria-associated payload at the non-hypoxic delivery location is not at the selected non-bacteria-associated concentration value, the concentration controlling mechanisms may be activated to adjust concentration of the non-bacteria-associated payload at the non-hypoxic delivery location. Similarly, if concentration of the released bacteria-associated payload at the hypoxic delivery location is not at the selected bacteria-associated concentration value, the concentration controlling mechanisms may be used to adjust concentration of the bacteria-associated payload at the hypoxic delivery location. However, if concentration of the released non-bacteria-associated payload at the non-hypoxic delivery location is at the selected non-bacteria-associated concentration value and concentration of the released bacteria-associated payload at the hypoxic delivery location is at the selected bacteria-associated concentration value, a tumor response may be determined using techniques generally known in the art. If the tumor response is not complete, untreated regions of the target tumor may be identified and an additional dose of the non-bacteria-associated nanoparticle component and/or the bacteria-associated nanoparticle component may be delivered to the untreated regions.

According to other embodiments of the present invention, a system for image-guided delivery of a nanoparticle mixture to a target tumor located in a region of interest comprises an imaging device configured to acquire a plurality of pre-operative images of the region of interest and a computer system. The computing system is operably coupled to the imaging device and includes a planning system, a guidance subsystem, and a quantification subsystem. The planning subsystem is configured to utilize the pre-operative images of the region of interest to (i) select a mixture of bacteria linked and non-linked nanoparticles, (ii) identify one or more delivery locations within the regions of interest for delivery of the mixture, and (iii) generate a planned path for delivering the mixture to one or more delivery locations. The guidance subsystem is configured to (i) utilize the pre-operative images of the region of interest to monitor a current location of a delivery device delivering the mixture to one or more delivery locations, and (ii) update the planned path based on the current location of a delivery device. In some embodiments, the guidance subsystem is further configured to utilize the pre-operative images of the region of interest to (i) determine one or more payload release locations for the mixture of bacteria linked and non-linked nanoparticles; and (ii) provide guidance to a user for placement of a hyperthermia applicator at the one or more release locations.

In some embodiments, the aforementioned quantification subsystem is configured to utilize the pre-operative images of the region of interest to generate a distribution of the bacteria linked and non-linked nanoparticles of the mixture in the region of interest. The quantification subsystem generates the distribution of the bacteria linked and non-linked nanoparticles of the mixture in the region of interest based on, for example, a correlation between (i) image intensity or a measurement derived from image intensity and (ii) concentration of the bacteria linked and non-linked nanoparticles.

Aside from the various subsystems discussed above, in some embodiments, the computing system further comprises a controlled activation subsystem configured to (i) utilize the pre-operative images of the region of interest to monitor state change of the bacteria linked and non-linked nanoparticles of the mixture and (ii) control concentration of the bacteria linked and non-linked nanoparticles of the mixture using the imaging device.

According to other embodiments of the present invention, an article of manufacture for image-guided delivery of a nanoparticle mixture to a target tumor located in a region of interest comprises a non-transitory, tangible computer-readable medium holding computer-executable instructions for performing the aforementioned method discussed, with or without the additional features described above.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses related to image-guided magnetic trap controlled delivery of a mixture of bacteria and non-bacteria linked nanoparticles. As described in further detail below, the technique described herein employ the following steps: (1) planning and guidance of the delivery of such nanoparticles that are image-able under a real-time modality such as Magnetic Resonance (MR), Ultrasound (US), or X-ray, (2) quantification of the delivery, (3) application of a stimulus for a controlled release of cytotoxin from the nanoparticle (4) continuous monitoring under a real-time modality to determine the portion of particles that have released their payload, (5) redirecting or addition of further dose of nanoparticles to areas that may not have received adequate dose, and (6) trapping and control of the these mixtures using a trap created by use of magnetic gradients (or similar modality-specific trapping mechanisms in the case of non-magnetic image acquisition). These various steps are repeated in a closed-loop feedback manner until the desired dose required for full treatment is delivered.

The basic nanoparticle mixture used with the techniques described herein comprise two components, namely, the non-bacteria-associated nanoparticle (component A) and bacteria-associated nanoparticle (component B). Each component of the nanoparticle is associated with a carrier structure made from a liposomal or polymer composition to carry a drug payload. Additionally the carrier structure contains a contrast agent enabling visualization of aggregates of these nanoparticles under a suitable modality such as MR or US. Such contrast agents are generally known in the art and, thus, these agents are only described here briefly. The agent may vary depending on the imaging modality. For example, paramagnetic or super-paramagnetic materials such as gadolinium or iron oxide are a suitable choice if MR is used, while gaseous agents such as per-fluropentane (PFP) are a suitable choice for US. The added advantage of using iron-oxide is that it can double-up as the controlling handle for managing the concentration of the nanoparticle by the control activation subsystem (as described in further detail below). The carrier structure is designed to be heat sensitive, that is, with an elevation of temperature above the nominal body temperature, these carriers are forced to release their payload. This required thermal elevation is designed in the range of 42-43 degrees Celsius.

Figure 1:
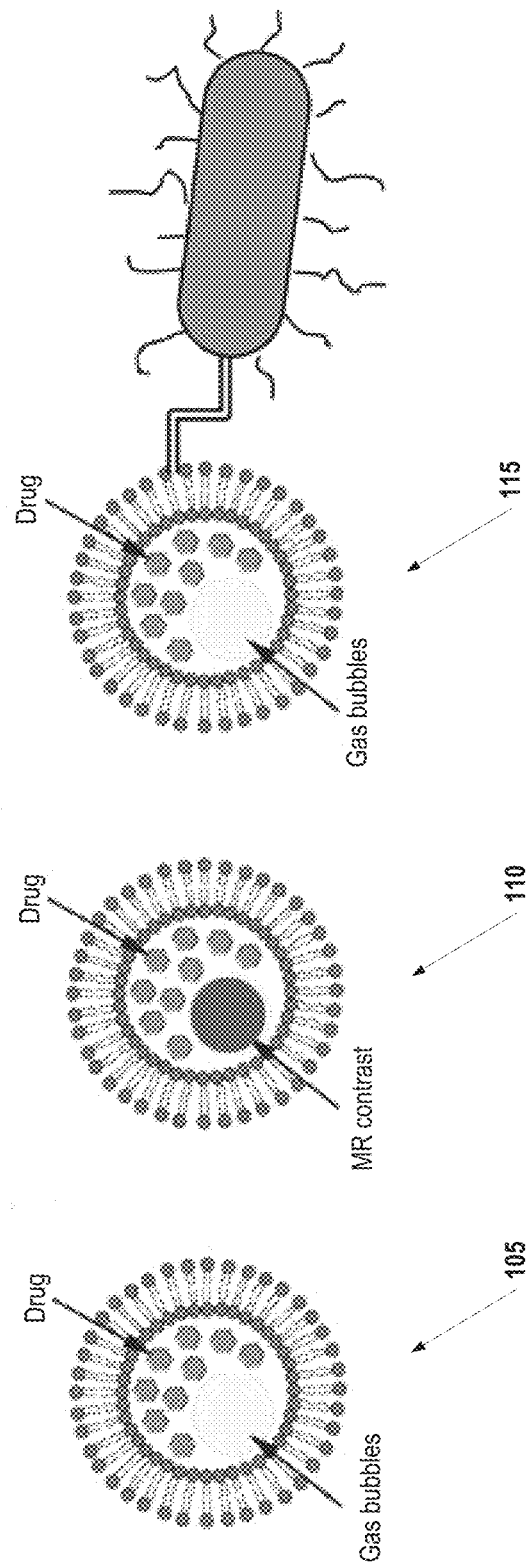
FIG. 1 presents an illustration of nanoparticles that may be utilized in some embodiments.

FIG. 1 presents an illustration of nanoparticles that may be utilized in some embodiments. In the figure, Image 105 shows an illustration of a non-linked US image-able liposomal nanoparticle. Image 110 provides an illustration of a non-linked MR image-able nanoparticle. Finally, Image 115 shows a bacteria-linked US image-able liposomal nanoparticle. The techniques described herein may be applied to polymer coated nanoparticles, in which case the polymer coating is used in a lipid bilayer. The bacteria's flagella provide an active means of transport within the tumor micro-environment.

Figure 2:
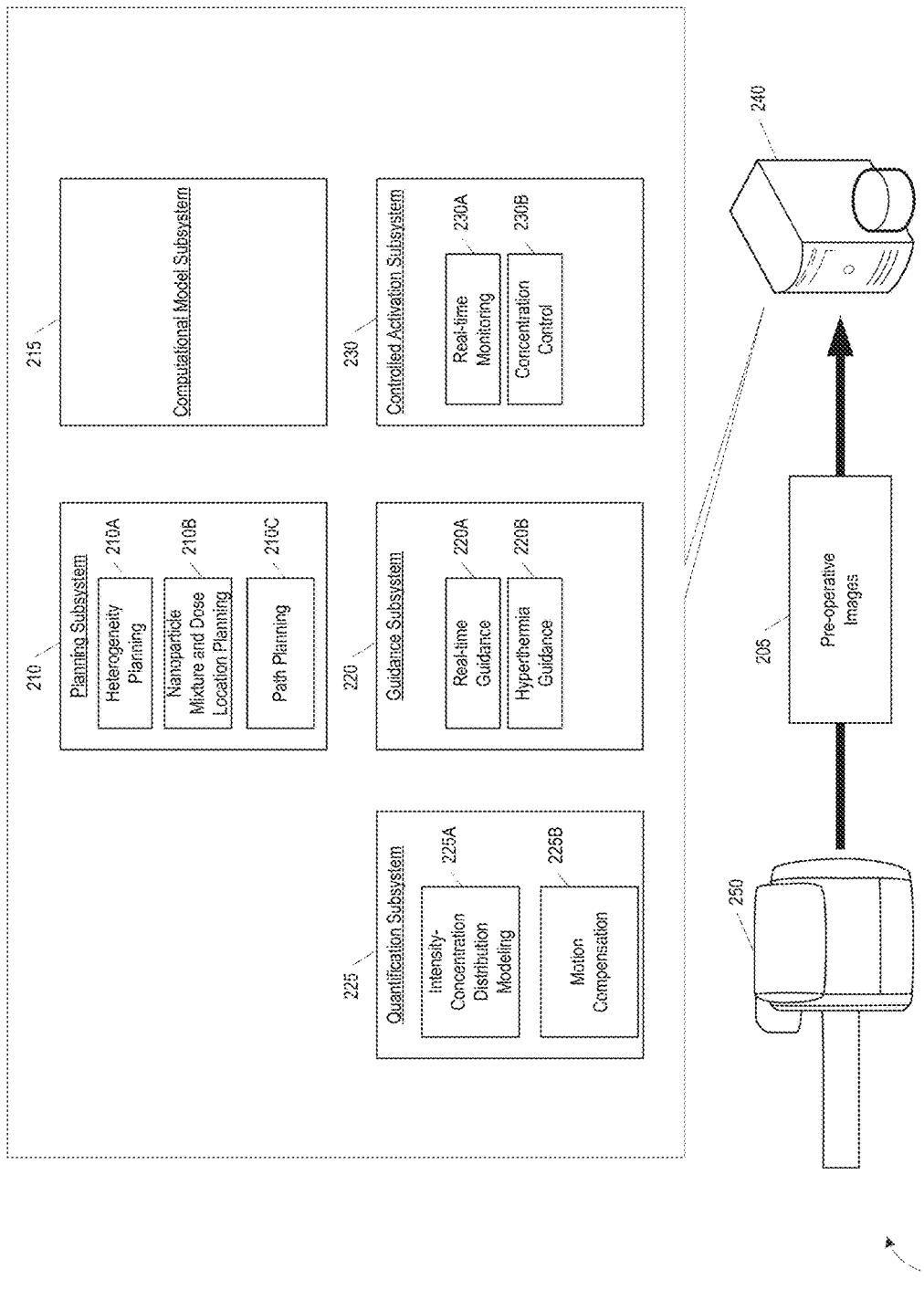
FIG. 2 illustrates a system for image-guided magnetic trap controlled delivery of a mixture of bacteria and non-bacteria linked nanoparticles, according to some embodiments.

FIG. 2 illustrates a system 200 for image-guided magnetic trap controlled delivery of a mixture of bacteria and non-bacteria linked nanoparticles, according to some embodiments. Briefly, system 200 comprises an Imaging Device 250 which acquires pre-operative images 205 of a region of interest which includes the target tumor. In the example of FIG. 2, a magnetic resonance imaging scanner is shown; however, it should be understood that the Imaging Device 250 may implement a different imaging modality in other embodiments of the present invention. To monitor and control delivery of a mixture of bacteria and non-bacteria linked nanoparticles to the tumor, the pre-operative images 205 are provided to a Computing System 240 which includes a plurality of subsystems 210, 215, 220, 225, and 230 which facilitate image-guided planning, guidance, monitoring and control of delivery of the mixture. Each of these subsystems may be implemented using any combination of software and hardware. For example, in some embodiments each subsystem is implemented as a software library comprising one or more modules to provide specific functionality relevant to delivery of the mixture. Each of these subsystems 210, 215, 220, 225, and 230 and their corresponding modules are described in greater detail below.

The Planning Subsystem 210 shown in FIG. 2 takes the pre-operative images 205 and produces a plan which specifies the ratios of the mixture of the nanoparticles and the location at which they should be delivered within the patient.

The Planning Subsystem 210 comprises a Heterogeneity Planning module 210A. Typically, a target tumor would have non-hypoxic regions that are nutrient rich and have an adequate supply of blood of irregular vasculature and a hypoxic region without much vasculature. The Heterogeneity Planning module 210A determines the location and extent of these regions. Additionally, the Heterogeneity Planning module 210A segments these regions and identifies their respective volumes. Vascular regions are identified by a large uptake of contrast agent whereas non-hypoxic region appear un-contrasted in such images.

The Planning Subsystem 210 further comprises a Nanoparticle Mixture and Dose Location Planning module 210B. Once the extent and relative size of the regions are determined by the Heterogeneity Planning module 210A, the ratio of bacteria linked and non-linked nanoparticles that need to be delivered is computed by a Nanoparticle Mixture and Dose Location Planning module 210B using a computational model of drug distribution achieved by both these components. The transport mechanism for each is factored in to this computation. This also determines the ideal location for the delivery of each of the components. Typically, the bacteria linked nanoparticle will be delivered intra-tumorally close to the hypoxic region to be treated. The predominant transport mechanism is the gradient in the micro-environment of the tumor which causes a migration of the bacteria linked nanoparticles to non-hypoxic regions. On the other hand, the predominant transport mechanism for the non-bacteria linked nanoparticles is diffusion. Thus, these must be delivered intra-vascularly in the vicinity of non-hypoxic regions.

Accurate delivery of the nanoparticles is essential to achieve delivery of full dosage in tumor. To facilitate accurate localization of the delivery devices that carry the nanoparticles to the tumor, a Path Planning module 210C included in the Planning Subsystem 210 provides image-guided navigation. For the catheter delivery device, the Path Planning module 210C provides a feasible vessel path from the entry point of the catheter to the target locations. For the needle delivery device, the Path Planning module 210C provides an entry point(s) and target locations for the needles. The entry point is determined to minimize the number of punctures of the needle and the number of readjustments required to cover the entire tumor.

The Guidance Subsystem 220 shown in FIG. 2 comprises a Real-time Guidance Module 220A which provides real-time updates and corrections to the planned path based on intra-operative imaging and the current location of the delivery device. This module factors in the motion of the target due to physiological factors such as breathing. The nanoparticles that are used with the techniques described herein are designed to release their payload on application of mild hyperthermia. Several techniques are generally known in the art to apply hyperthermia including use of energy sources such as radio-frequency, microwave and focused ultrasound. Irrespective of the energy source, two considerations are essential to ensure proper release of the nanoparticles payload, namely, the location of the applicator and temperature of environment.

The Guidance Subsystem 220 further comprises a Hypothermia Guidance Module 220B which is configured to determine and guide the user to place the hyperthermia applicator at the correct location. A computational model for heating of the tumor micro-environment that factors in heat loss due to diffusion, blood flow and thermal property variations between hypoxic and non-hypoxic regions (typically, non-hypoxic regions are good conductors of heat, whereas hypoxic regions are not) is used to determine optimal location.

The Quantification Subsystem 225 in FIG. 2 is a component of the drug-delivery mechanism which utilizes a mixture of bacteria-linked and non-linked nanoparticles. The Quantification Subsystem 225 takes as input real-time macroscopic volumetric images and produces the distribution of these nanoparticle aggregates in the region of interest. This is achieved by the design of the nanoparticle making their aggregates image-able under a specific modality and the following two modules: an Intensity-Concentration Distribution Modeling module 225A and Motion Compensation module 225B.

As the nanoparticle carrier contains a suitable contrast agent such as iron-oxide for MR image-ability or PFP gas bubble for US image-ability, aggregates of such nanoparticles appear as dark and bright spots in MR or US, respectively. The peak intensity is a function of the concentration, blood flow, physiological motion and the state of the nanoparticle carriers. If the image intensity is integrated over a time period, for instance, by computing the area under the intensity-time curve, from t=0 to t=$t_p$, where $t_p$ is time to peak, then this integral value is just the function of regional concentration and the state of the nanoparticle carriers. Since the state of the nanoparticle is known (see below), the intensity correlates to concentration. Thus, this image intensity-concentration can be determined by the Intensity-Concentration Distribution Modeling module 225A ex-vivo prior and normalized. An offline normalized intensity-concentration calibration curve is sufficient, as the key indicator is the relative change in intensity from the baseline image to determine if sufficient nanoparticles have reached the target region.

Since intensity of nanoparticles is dependent on blood flow and an integral quantity is desired, it is important to factor in the physiological motion of the target and compensate for this motion during the integration step. In some embodiments, the Motion Compensation module 225B determines the motion of each region of interest using motion estimation techniques such as optical flow and determines the intensity-time profile for each voxel independently. In other embodiments, the Motion Compensation module 225B solves for the intensity-time profile for each voxel in conjunction with the neighboring voxels. Thus, the problem is formulated as fitting T observations of voxel intensity I(x, t) to a parametric function $f(x, t; y)$, regularized by the total variation of $f(x, t; y)$ in the voxel neighborhood N:

$$f^*(x, t; y) = \min_y \left[ \sum_{x \in V, t \in T} \|I(x, t) - f(x, t; y)\| + \sum_{x \in V, t \in T} \sup \sum_{x \in N} |f(x, t; y)| \right].$$

Here, x is the location of the voxel, t is time and y are the parameters of the function $f$.

A Controlled Activation Subsystem 230 in the system 200 comprises a Real-Time Monitoring Module 230A configured to provide real-time monitoring of nanoparticle state changes. An important aspect for nanoparticle based drug delivery is to reach and maintain the optimal temperature required for the heat-sensitive nanoparticles to release their payload. Both MR and US based thermal monitoring is established in literature and can be used for this purpose. The goal of thermometry is to identify the ratio of nanoparticles that have changed state and delivered their payload. However, in our approach we can use the novel aspect of the nanoparticle design that is its ability to influence the intensity of MR or US when its state changes and it has released its payload, to directly determine the fraction of nanoparticles that have released their payload. This guidance module utilizes this property, the heat computational model and the prior history of hyperthermia application to monitor the distribution of the nanoparticles' state. It then guides the user to redeploy the hyperthermia applicator if necessary.

The Controlled Activation Subsystem 230 further comprises a Concentration Control module 230B configured to control the concentration of nanoparticles. It is generally known in the art that tumors have "leaky" vasculature that allows molecules below a certain threshold to diffuse into the interstitial region. This would allow the non-linked nanoparticles to diffuse into the vasculature rich compartment of the tumor. Likewise, the nutrient gradients in the micro-environment of the tumor would cause the bacteria-linked nanoparticles to migrate to the vasculature deficient/hypoxic region. These passive modes of transport though preferred, may sometimes be slow or non-existent, which in turn may result in under dosage regions. The added benefit of quantification is that such a situation can be identified in-vivo and corrective action can be applied. If sufficient nanoparticles of the correct type are present elsewhere in the tumor, they can be manipulated to reach the under dosed part. In case no such area exists, additional nanoparticles can be injected at the appropriate location. The Concentration Control module 230B provides means to achieve the former, which is referred to herein as "active transport".

The principle of "active transport" is based on creation of suitable gradients that would force the nanoparticles to move along a particular direction. This direction is determined by the analysis of the quantification information and points from the area of high concentration to that of low concentration of nanoparticles. In case of MR, this gradient force is generation by application of suitable modulating pulses on the imaging coils superimposed or interleaved with the imaging pulses. This gradient force creates a magnetic trap that would trap these particles with a region that can be specified on the guidance images. In one embodiment, this is the entire tumor or a suitable compartment of the tumor which is under-dosed. In some embodiments, magnetic trap can be generated from using the coils for MR imager or from an external field generator.

In case of US, modulation of intra-tumoral pressure is achieved by application of a pulse train of medium intensity (greater than used for imaging, but less than used for hyperthermia/cavitation) ultrasound waves. The net desired effect is to create a high pressure spot in the region of high concentration, and a low pressure region in the areas of low concentration of nanoparticles. The pressure force gradient creates an acoustic trap that would trap these particles with a region that can be specified on the guidance images. In one embodiment, this is the entire tumor or a suitable compartment of the tumor which is under-dosed.

The Computational Modeling Subsystem 215 comprises a plurality of models which provide information to the other subsystems 210, 220, 225, and 230 included in the system 200. Thus, these models may be used to determine information such as: the distribution of the components of the nanoparticle mixture in each of the compartments of the tumor given the cite and dosage of the delivery; the image intensity distribution given a distribution of the components of the nanoparticle mixture; the distribution of heat given the location and type of hyperthermia applicator; the distribution of the nanoparticle carriers and their respective states given their original distribution and the heat distribution; the strength of active transport gradients and the redistribution of the nanoparticles given the type of energy source and the original distribution; and the lethal dose delivered to the tumor cells given the distribution of the nanoparticles and respective states. To compute these models, the Computational Modeling Subsystem 215 may use a multi-component, multi-scale computational model involving modeling of processes such as particle diffusion, heat transfer via diffusion and convection, bacteria chemotransport, bacteria flagella locomotion, bacteria growth, ultrasound propagation in tissue, electro-magnetic fields in tissue, cell death via temperature elevation, apoptosis, and nanoparticle carrier response to temperature elevation.

Figure 3:
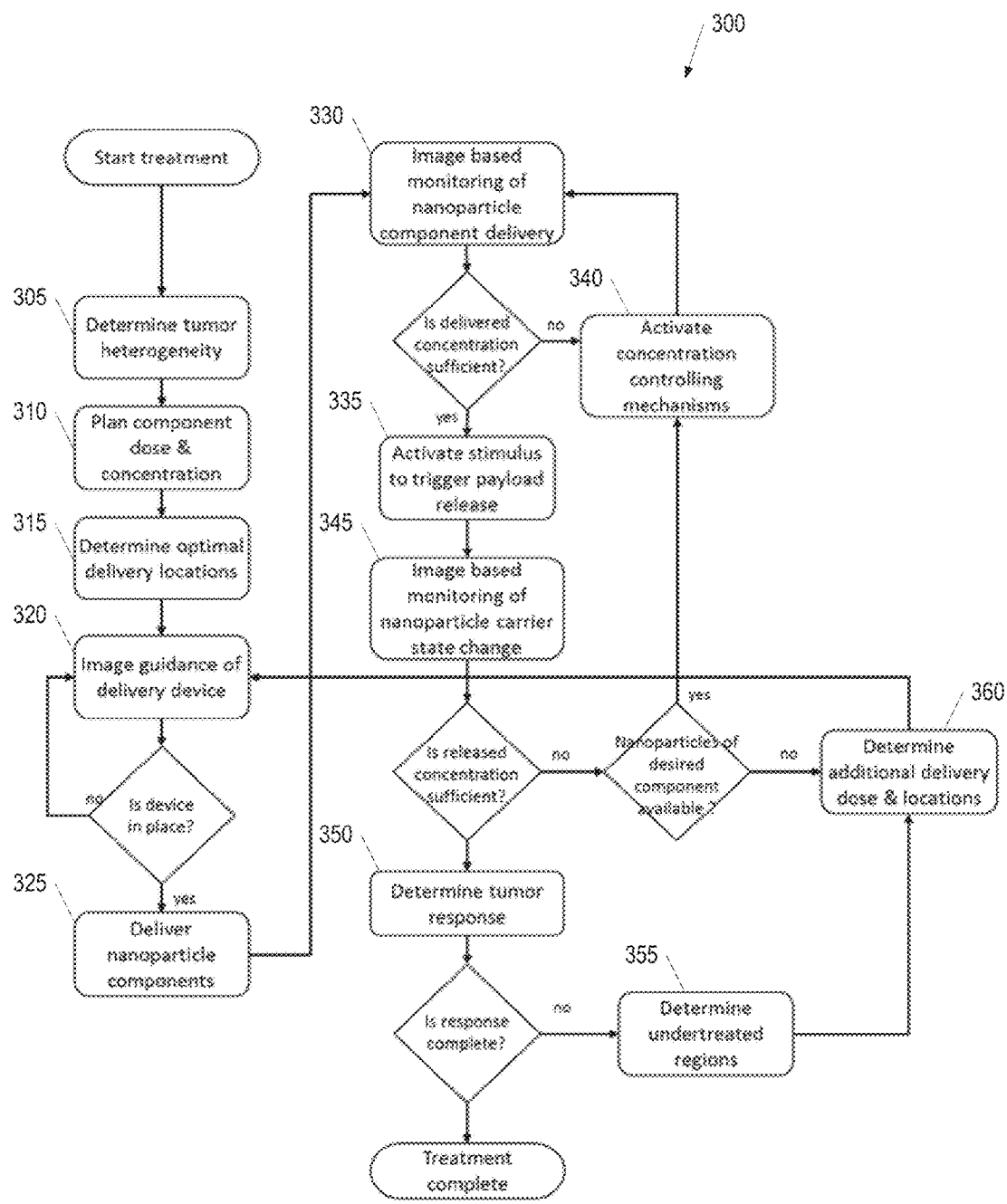
FIG. 3 illustrates a process for implementing guided magnetic trap controlled delivery of a mixture of bacteria and non-bacteria linked nanoparticles, according to some embodiments.

FIG. 3 illustrates a method 300 for implementing guided magnetic trap controlled delivery of a mixture of bacteria and non-bacteria linked nanoparticles, according to some embodiments. The process begins at step 305 with determination of heterogeneity of the target tumor, which is then used to plan the component dose/concentration of the nanoparticle mixture at step 310. Next, at step 315, the locations of the delivery points for each of the mixture components are determined. The ideal location to deliver the dose may be different for each component. The non-bacteria-associated component (component A) of the nanoparticle mixture may be delivered to one or more feeding vessels of the tumor. The feeder vessel can be determined using a simplistic approach based on proximity of the tumor region. Alternatively, the feeder vessels can be determined from a computational flow model that factors in the heterogeneity of the target tumor. The bacteria-associated component (component B) of the nanoparticle mixture can be injected intra-tumorally if the hypoxic region is in the central core and farther from vessel boundaries or at the same location as component A by using an intra-vascular catheter. In some embodiments, the location and optimal delivery dose may be determined by the Planning Subsystem 210 described above with reference to FIG. 2.

Because, in this application, the location of the delivery is important, real-time images are used at steps 320-330 for guidance and confirmation of location of delivery. These real-time images (e.g., acquired from an MR imager or a US system) may be co-registered to one or more modules in the Planning Subsystem 210 (see FIG. 2). Specifically, at step 320 the images are used for guidance of the initial insertion of the delivery device (e.g., a catheter or needle). Note that there is a feedback loop that is used to repeat step 320 until the delivery device is in place. Then, as the delivery device is manipulated during delivery of the nanoparticle components at step 325, its location can be visualized and monitored on the planning images at step 330. Alternatively, in other embodiments, location sensors (e.g., optical, inertial or magnetic) that report the position of the tip of the delivery device can be embedded in the device itself. In these embodiments, the co-ordinate systems of the tracking sensor system are calibrated to the planning images prior to the start of the procedure. Once the delivery device is at the planned location, the delivery of the nanoparticles can be started.

For all parts of the tumor to get adequate dose, it is necessary that the concentration of each of the components of the nanoparticles reaches a pre-determined threshold. The nanoparticles are made image-able to enable quantification of their concentration. The intensity observed in the real-time image from MR scan or US scan is correlated to the concentration and distribution using a prior model. Motion compensation is applied to the real-time images to correct for the region of interest's physiological motion such as from breathing. This is essential to separate the drop in intensity that may occur due to motion from the drop of intensity due to wash out of nanoparticles that may occur in the vasculature rich compartments. Since we would like to maintain suitable ratios of both the components of the nanoparticles in the overall tumor region, the controlled activation subsystem is required to monitor and control the concentration of these nanoparticles at step 340. The mechanism of controlling the concentration is dependent on the modality used and is described above with reference to the Concentration Control module 230B shown in FIG. 2. Once adequate concentration is reached for both the components, a controlled stimulus is applied at step 335 that would force the carrier attached to the nanoparticle to release its payload. This may be achieved by mild hyperthermia of the target region. The methods to achieve mild hyperthermia are described above with reference to the Hypothermia Guidance module 220B shown in FIG. 2.

An important consideration in the design of the image-able nanoparticles is the ability to monitor the portion or ratio of nanoparticles that have changed their state and released their payloads in the respective tumor compartments. This monitoring is performed at step 345. In embodiments where MR scan is employed for monitoring, step 345 may be accomplished by determining the difference in magnetic permeability of the contrast agent in the encapsulation states. Once the carrier structure releases its payload, the contrast agent is no longer encapsulated in the carrier structure. In embodiments where US is used, step 345 may be accomplished by determining the difference in the acoustic impedance between the carrier states.

Finally, at step 350 a computational dose modeling system determines the total cytotoxin concentration delivered to the entire tumor and its various compartments. This model factors in the heterogeneity, transport mechanism, cell death mechanism, real-time feedback from the image-able nanoparticles and the concentration of both components of nanoparticles in encapsulated as well as released carrier states. Portions of the tumor that are suspect of under treatment are identified at step 355. The controlling mechanism of Controlled Activation Subsystem 230 (See FIG. 2) is activated if the encapsulated drug of the correct nanoparticle component (A or B) is available. If this is not the case, a new dose and optimal delivery location is identified at step 360 for further injection of this component. This procedure is repeated until entire tumor has received adequate therapeutic dose.

Figure 4:
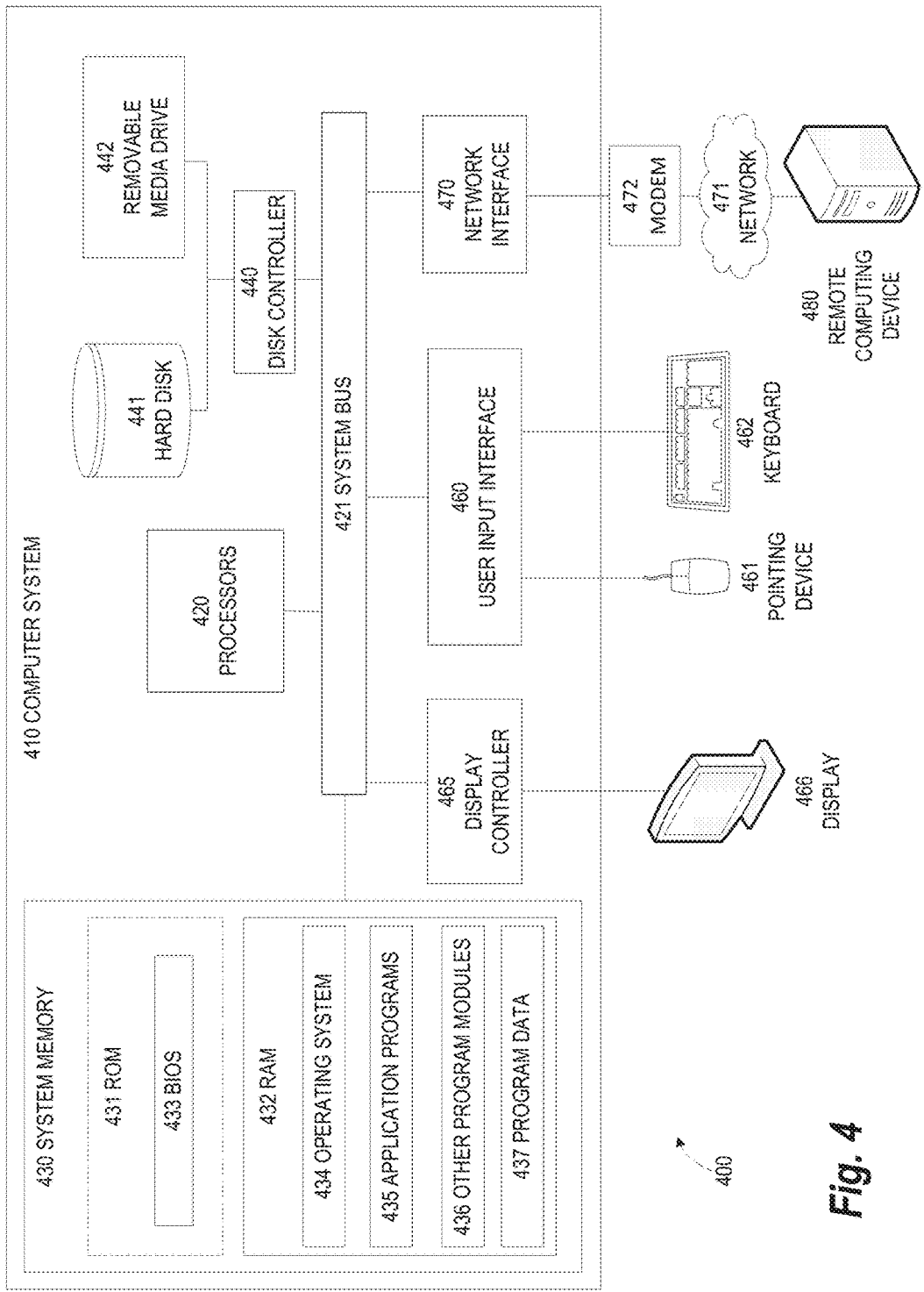
FIG. 4 illustrates an exemplary computing environment within which embodiments of the invention may be implemented.

FIG. 4 illustrates an exemplary computing environment 400 within which embodiments of the invention may be implemented. In some embodiments, the computing environment 400 may be used to implement one or more of the subsystems illustrated in the system 200 of FIG. 2. Additionally, this computing environment 400 may be used to implement the method 300 described above with respect to FIG. 3. Computers and computing environments, such as computer system 410 and computing environment 400, are known to those of skill in the art and thus are described briefly here.

As shown in FIG. 4, the computer system 410 may include a communication mechanism such as a bus 421 or other communication mechanism for communicating information within the computer system 410. The computer system 410 further includes one or more processors 420 coupled with the bus 421 for processing the information. The processors 420 may include one or more central processing units (CPUs), graphical processing units (GPUs), or any other processor known in the art.

The computer system 410 also includes a system memory 430 coupled to the bus 421 for storing information and instructions to be executed by processors 420. The system memory 430 may include computer readable storage media in the form of volatile and/or nonvolatile memory, such as read only memory (ROM) 431 and/or random access memory (RAM) 432. The system memory RAM 432 may include other dynamic storage device(s) (e.g., dynamic RAM, static RAM, and synchronous DRAM). The system memory ROM 431 may include other static storage device (s) (e.g., programmable ROM, erasable PROM, and electrically erasable PROM). In addition, the system memory 430 may be used for storing temporary variables or other intermediate information during the execution of instructions by the processors 420. A basic input/output system (BIOS) 433 containing the basic routines that helps to transfer information between elements within computer system 410, such as during start-up, may be stored in ROM 431. RAM 432 may contain data and/or program modules that are immediately accessible to and/or presently being operated on by the processors 420. System memory 430 may additionally include, for example, operating system 434, application programs 435, other program modules 436 and program data 437.

The computer system 410 also includes a disk controller 440 coupled to the bus 421 to control one or more storage devices for storing information and instructions, such as a hard disk 441 and a removable media drive 442 (e.g., floppy disk drive, compact disc drive, tape drive, and/or solid state drive). The storage devices may be added to the computer system 410 using an appropriate device interface (e.g., a small computer system interface (SCSI), integrated device electronics (IDE), Universal Serial Bus (USB), or FireWire).

The computer system 410 may also include a display controller 465 coupled to the bus 421 to control a display 466, such as a cathode ray tube (CRT) or liquid crystal display (LCD), for displaying information to a computer user. The computer system includes an input interface 460 and one or more input devices, such as a keyboard 462 and a pointing device 461, for interacting with a computer user and providing information to the processor 420. The pointing device 461, for example, may be a mouse, a trackball, or a pointing stick for communicating direction information and command selections to the processor 420 and for controlling cursor movement on the display 466. The display 466 may provide a touch screen interface which allows input to supplement or replace the communication of direction information and command selections by the pointing device 461.

The computer system 410 may perform a portion or all of the processing steps of embodiments of the invention in response to the processors 420 executing one or more sequences of one or more instructions contained in a memory, such as the system memory 430. Such instructions may be read into the system memory 430 from another computer readable medium, such as a hard disk 441 or a removable media drive 442. The hard disk 441 may contain one or more datastores and data files used by embodiments of the present invention. Datastore contents and data files may be encrypted to improve security. The processors 420 may also be employed in a multi-processing arrangement to execute the one or more sequences of instructions contained in system memory 430. In alternative embodiments, hard-wired circuitry may be used in place of or in combination with software instructions. Thus, embodiments are not limited to any specific combination of hardware circuitry and software.

As stated above, the computer system 410 may include at least one computer readable medium or memory for holding instructions programmed according to embodiments of the invention and for containing data structures, tables, records, or other data described herein. The term "computer readable medium" as used herein refers to any medium that participates in providing instructions to the processor 420 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 441 or removable media drive 442. Non-limiting examples of volatile media include dynamic memory, such as system memory 430. Non-limiting examples of transmission media include coaxial cables, copper wire, and fiber optics, including the wires that make up the bus 421. Transmission media may also take the form of acoustic or light waves, such as those generated during radio wave and infrared data communications.

The computing environment 400 may further include the computer system 410 operating in a networked environment using logical connections to one or more remote computers, such as remote computer 480. Remote computer 480 may be a personal computer (laptop or desktop), a mobile device, a server, a router, a network PC, a peer device or other common network node, and typically includes many or all of the elements described above relative to computer system 410. When used in a networking environment, computer system 410 may include modem 472 for establishing communications over a network 471, such as the Internet. Modem 472 may be connected to bus 421 via user network interface 470, or via another appropriate mechanism.

Network 471 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 410 and other computers (e.g., remote computer 480). The network 471 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 471.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method for image-guided delivery of a nanoparticle mixture to a target tumor located in a region of interest, the method comprising:
selecting a non-hypoxic delivery location within the region of interest for delivery of a non-bacteria-associated nanoparticle component included in the nanoparticle mixture;
selecting a hypoxic delivery location within the region of interest for delivery of a bacteria-associated nanoparticle component included in the nanoparticle mixture; and
performing an image-guided delivery and monitoring process, wherein intra-operative images of the region of interest are continually acquired and used to:
guide placement of a device into the non-hypoxic delivery location,
monitor delivery of the non-bacteria-associated nanoparticle component included in the nanoparticle mixture at the non-hypoxic delivery location,
guide placement of the device into the hypoxic delivery location, and
monitor delivery of the bacteria-associated nanoparticle component included in the nanoparticle mixture at the hypoxic delivery location.

2. The method of claim 1, further comprising:
selecting a bacteria-associated concentration value and a non-bacteria-associated concentration value based on a heterogeneity assessment of the target tumor;
if concentration of the non-bacteria-associated nanoparticle component at the non-hypoxic delivery location is below the selected non-bacteria-associated concentration value, using one or more concentration controlling mechanisms to adjust the concentration of the non-bacteria-associated nanoparticle component at the non-hypoxic delivery location; and
if concentration of the bacteria-associated nanoparticle component at the hypoxic delivery location is below the selected bacteria-associated concentration value, using the one or more concentration controlling mechanisms to adjust the concentration of the bacteria-associated nanoparticle component at the hypoxic delivery location.

3. The method of claim 2, wherein the intra-operative imaging of the region of interest is performed using a magnetic resonance imaging device and the one or more concentration controlling mechanisms comprise a magnetic trap created by applying a gradient force toward at least one of the hypoxic delivery location or the non-hypoxic delivery location.

4. The method of claim 3, wherein the magnetic trap is generated using one or more coils from the magnetic resonance imaging device.

5. The method of claim 3, wherein the magnetic trap is generated using one or more coils from an external field generator.

6. The method of claim 3, wherein the non-bacteria-associated nanoparticle component and the bacteria-associated nanoparticle component of the nanoparticle mixture each comprise a carrier structure which contains a paramagnetic material.

7. The method of claim 6, wherein the paramagnetic material comprises iron oxide and the paramagnetic material is utilized by the one or more concentration controlling mechanisms.

8. The method of claim 2, wherein the intra-operative imaging of the region of interest is performed using an ultrasound imaging device and the one or more concentration controlling mechanisms comprise an acoustic trap created by applying a pulse train of medium intensity ultrasound waves in a region of high concentration.

9. The method of claim 2, further comprising:
if concentration of the non-bacteria-associated nanoparticle component at the non-hypoxic delivery location is at the selected non-bacteria-associated concentration value, activating one or more stimuli to trigger release of a non-bacteria-associated payload included in the non-bacteria-associated nanoparticle component; and if concentration of the bacteria-associated nanoparticle component at the hypoxic delivery location is at the selected bacteria-associated concentration value, activating the one or more stimuli to trigger release of a bacteria-associated payload included in the bacteria-associated nanoparticle component.

10. The method of claim 9, wherein the one or more stimuli comprise an energy source which applies hyperthermia to at least one of the non-hypoxic delivery location and the hypoxic delivery location.

11. The method of claim 9, wherein the one or more stimuli comprise a magnetic field.

12. The method of claim 9, further comprising:
during the image-guided delivery and monitoring process, using the intra-operative images to monitor release of at least one of the non-bacteria-associated payload and the bacteria-associated payload.

13. The method of claim 10, further comprising:
if concentration of the released non-bacteria-associated payload at the non-hypoxic delivery location is not at the selected non-bacteria-associated concentration value, activating the one or more concentration controlling mechanisms to adjust concentration of the non-bacteria-associated payload at the non-hypoxic delivery location; and
if concentration of the released bacteria-associated payload at the hypoxic delivery location is not at the selected bacteria-associated concentration value, activating the one or more concentration controlling mechanisms to adjust concentration of the bacteria-associated payload at the hypoxic delivery location.

14. The method of claim 10, further comprising:
if concentration of the released non-bacteria-associated payload at the non-hypoxic delivery location is at the selected non-bacteria-associated concentration value and concentration of the released bacteria-associated payload at the hypoxic delivery location is at the selected bacteria-associated concentration value, determining a tumor response.

15. The method of claim 14, further comprising:
if the tumor response is not complete, identifying one or more untreated regions of the target tumor; and initiating delivery of an additional dose of at least one of the non-bacteria-associated nanoparticle component and the bacteria-associated nanoparticle component at the one or more untreated regions.

* * * * *